United States Patent [19]

Wolfson et al.

[11] Patent Number: 5,022,261
[45] Date of Patent: Jun. 11, 1991

[54] ANEROID VOLUME DETERMINING SYSTEM

[76] Inventors: Jason Wolfson, 6 Greenwood Village, Easton, Mass. 02356; William Wolfson, 188 Pelham Island Rd., Wayland, Mass. 01778

[21] Appl. No.: 460,747

[22] Filed: Jan. 4, 1990

[51] Int. Cl.$^5$ .............................................. G01F 17/00
[52] U.S. Cl. .......................................... 73/149; 73/433
[58] Field of Search ....................... 73/149, 37.5, 433; 364/564

[56] References Cited

U.S. PATENT DOCUMENTS

| | | | |
|---|---|---|---|
| 3,769,834 | 11/1973 | Fletcher et al. | 73/149 |
| 4,095,473 | 6/1978 | Butchelor et al. | 73/433 |
| 4,144,749 | 3/1979 | Whitmore | 73/149 |
| 4,184,371 | 1/1980 | Brachet | 73/149 X |
| 4,369,652 | 1/1983 | Gundlach | 73/149 |
| 4,449,406 | 5/1984 | van Haren | 73/433 |
| 4,640,130 | 2/1987 | Sheng et al. | 73/149 X |
| 4,713,966 | 12/1987 | Thyren et al. | 73/149 |
| 4,866,991 | 9/1989 | Tse | 73/37.5 X |

OTHER PUBLICATIONS

*Exercise Physiology:Energy, Nutrition and Human Performance;* 2nd et. McArdle, Katch & Katch; Lea & Febiger-Philadelphia 1986; pp. 490-512.
Brown et al., "Influence of Abdominal Gas on the Boyle's Law Determination of Thoracic Gas Volume", The American Physiological Society, 1978, pp. 469-473.
Brozek, Josef, "Introductory Comment", pp. 640-641.
Donnelly et al., "Hydrostatic Weighing Without Head Submersion", Pub. by Jan. 1990, Known by May 1989.
Falkner, Frank, "An Air Displacement Method of Measuring Body Volume in Babies: A Preliminary Communication", pp. 75, 78, 79; Annals New York Academy of Sciences; Pub. by Jan. 1990.
Garrow, J. S., "New Approaches to Body Composition, The American Journal of Clinical Nutrition", May 1982, pp. 1152-1158.
Garrow et al., "A New Method for Measuring the Body Density of Obese Adults", The Nutrition Society, 1979, pp. 173-183, Br. J. Nutri, vol. 42.
Lim, Thomas P., "Critical Evaluation of the Pneumatic Method for Determining Body Volume: Its History and Technique", pp. 72-74; Annals New York Academy of Sciences; Pub. by Jan. 1990.
Lukashi, Henry C., "Methods for the Assessment of Human Body Composition: Traditional and New", American Society for Clinical Nutrition, 1987, Am. J. Clin Nutr., vol. 46; pp. 537-556.
Robertson, Jr. et al., "Lung Volumes in Man Immersed to the Neck: Dilution and Plethysmographic Techniques", pp. 679-682; pub. by Jan. 1990.

*Primary Examiner*—Tom Noland
*Attorney, Agent, or Firm*—Joseph S. Iandiorio

[57] ABSTRACT

An aneroid volume determining system includes an airtight chamber for holding a subject whose volume is to be detected; a volume adjuster including an inflatable container for varying the pressure in the chamber; sensing equipment including a pressure transducer for sensing the pressure in the chamber in the deflated and inflated states of the container; and controlling equipment, which can calculate the volume of the subject in response to the pressure sensed in the chamber with and without the subject present in the chamber and which equipment provides control signals to the volume adjuster for automatically controlling the inflation and deflation of the inflatable container.

17 Claims, 3 Drawing Sheets

ANEROID VOLUME DETERMINING SYSTEM

FIELD OF INVENTION

This invention relates to an aneroid volume determining system and more particularly to such a system which can be used to calculate density, body fat and lean body mass.

BACKGROUND OF INVENTION

The most accurate current method to measure body composition is water immersion densitometry. Water immersion densitometry is based on Archimedes' Principle, which states that the buoyancy force on an object submerged in water equals the weight of the water the object displaced. By determining the mass of an object dry, and then in water, the difference, divided by the density of the water, is the volume of the object. Once volume is determined by water immersion, that person's "residual" lung volume must be entered into the equation. The residual lung volume is the volume of the air still in the lungs of the submerged person, and must be known to accurately determine body composition. With the total volume of the person known, weight is measured, and from an equation describing human body composition based on density, the body fat content and lean body mass are calculated.

The drawbacks of water immersion densitometry are that it is a lengthy and uncomfortable process. It requires the person to be at ease in the water, and be able to remain underwater after exhaling all the air from his or her lungs. The residual lung volume test is also lengthy and uncomfortable. The equipment to perform this test is expensive and has a great maintenance cost associated with it. The reported accuracy of water immersion densitometry is ±2%. Air immersion has been suggested, but the cylinders and pistons and the associated equipment necessary to operate these devices make them unattractive also.

The cheapest and most popular method of determining body fat content is the "Calipers" method. In this test the person's skin is pinched in several places and the thickness of the layer of skin and subcutaneous fat is measured with a caliper. From a look-up table based on sex and age, one's body fat content is determined. This method is cheap, comfortable and easy. However, the accuracy is only reported to be ±10%, and the repeatability is questionable.

Another method is based on bioelectric impedance measurements. In this method an electrical current is passed through the body and the body's reactances are measured, for reactance is influenced by the amount of subcutaneous fat. A computer uses this result to calculate body fat content. The reported accuracy is less than water immersion and is heavily affected by body water retention at the time of the test.

Yet another method is based on infrared measuring, where an infrared beam is directed into the skin on a person's writing arm biceps. The muscle tissue reflects the infrared beam allowing the thickness of the subcutaneous fat to be measured in that one spot. A computer then determines body fat content based on this fat thickness sample and some general fitness questions asked of the person being measured. This method is not considered to be very accurate.

There are other methods of determining body composition including photon absorption, tomography, magnetic resonance, and dissection, which are even less appealing due to complexity, cost and/or difficulty.

SUMMARY OF INVENTION

It is therefore an object of this invention to provide an improved, simpler and less expensive volume determining system.

It is a further object of this invention to provide an improved aneroid volume determining system.

It is a further object of this invention to provide a volume determining system which operates quickly, comfortably and without water immersion.

It is a further object of this invention to provide such a system which is indifferent to the presence of ordinary clothing and does not require any special procedure to accommodate for residual lung capacity.

It is a further object of this invention to provide such a system which is inexpensive to build and to maintain yet is highly accurate.

This invention features an aneroid volume determining system having an airtight chamber for holding a subject whose volume is to be detected. A volume adjuster includes an inflatable container for varying the pressure in the chamber. There are means for sensing including a pressure transducer for sensing the pressure in the chamber in the deflated and inflated states of the container. There are also control means which include means for calculating the volume of the subject in response to the detection by the means for sensing of the pressure in the chamber with and without the subject present in the chamber.

In a preferred embodiment, the volume adjuster includes a fixed support within the container for defining the minimum volume of the container in the deflated state, and a fixed cavity external to the container for defining the maximum volume of the container in the inflated state. The container may be a balloon or some other device such as a diaphragm or pleated container. The volume adjuster means may also include pump means for inflating the container and valve means for controlling the inflating and deflating of the container. There may be a fill sensor for indicating when the container is fully inflated. The means for sensing may include a temperature sensor for sensing the temperature in the chamber and a humidity sensor for sensing the humidity in the chamber. There may also be means for determining the weight of the subject in the chamber and for converting weight to mass. The control means may include means for calculating the density of the subject from the weight or the mass and the volume, and for further calculating the percentage of body fat from the density, and then calculating the lean body weight from the total weight or mass and the percentage of body fat.

DISCLOSURE OF PREFERRED EMBODIMENT

Other objects, features and advantages will occur to those skilled in the art from the following description of a preferred embodiment and the accompanying drawings, in which.

Figure 1:
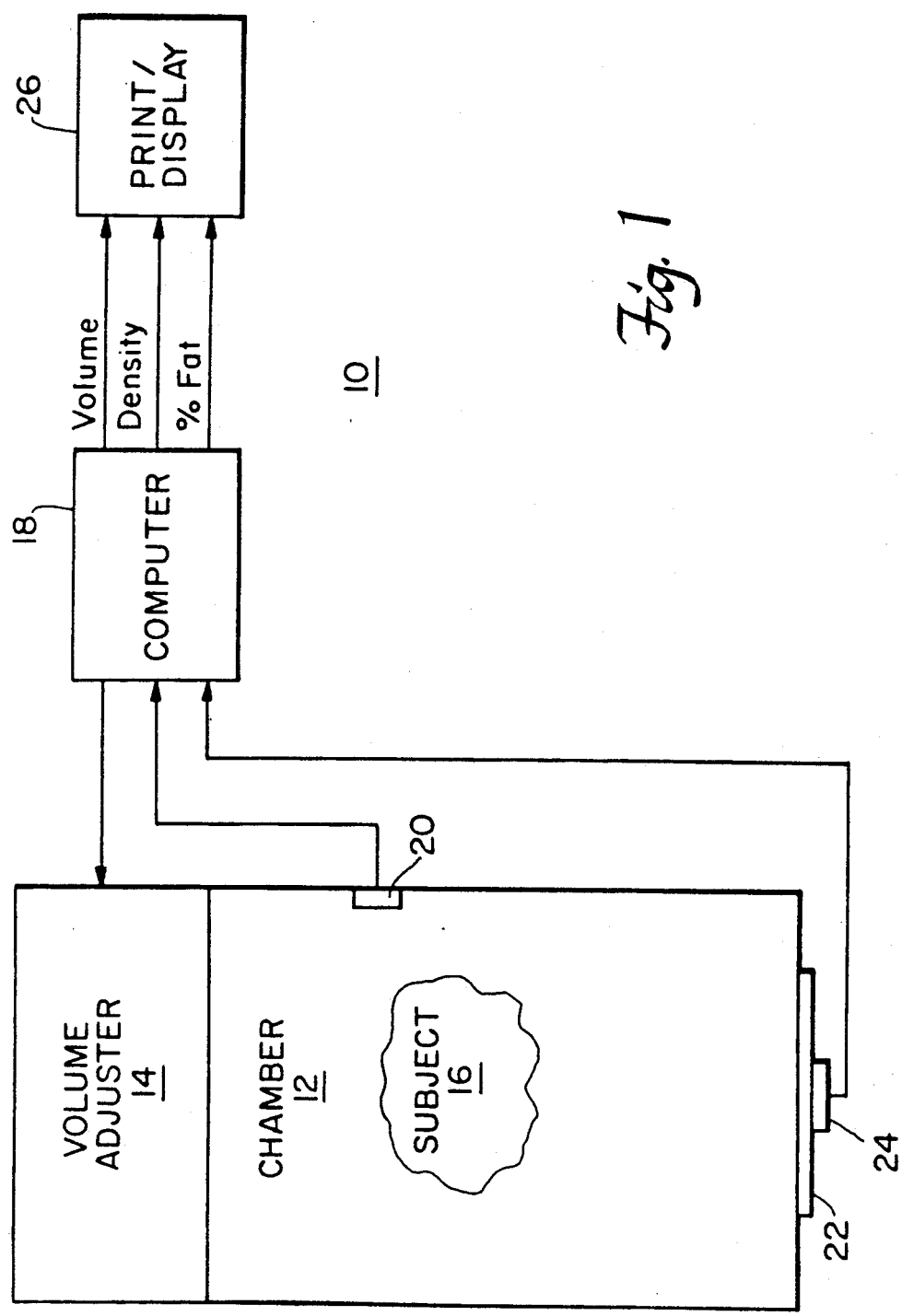
FIG. 1 is a diagrammatic view of a volume determining system according to this invention including apparatus for determining mass, density, percent of body fat and lean body weight.

The invention may be accomplished using an airtight chamber which holds a subject whose volume is to be detected. The subject can be a human, an animal, or an inanimate object. There is a volume adjuster including an inflatable container for varying the pressure in the chamber. This may be simply a balloon or an expanding diaphragm or pleated structure, whose volume increases and consequently decreases the residual volume of the chamber when the container is inflated. There is some means for sensing in the chamber including a pressure transducer for sensing the pressure in the chamber in the deflated and the inflated states of the container. There are control means, typically a computer, for calculating the volume of the subject in response to the detection by the means for sensing of the pressure in the chamber with and without the subject present. A fixed support such as a perforate bulbous structure may be disposed within the container, which may be a balloon for example, to define the minimum volume of the container in the deflated state. Surrounding the container or balloon, there may be a fixed cavity for defining the maximum volume of the container in the inflated state. For adjusting the volume, there is a pump to inflate the container and there are valves for controlling the input of air from the pump during the inflation cycle and for exhausting the container during the deflation cycle. A fill sensor may be provided proximate the outer cavity to indicate when the container is fully inflated. The temperature and humidity may also be sensed for more accurate volume detection, especially when there is a potential for variation in those qualities from cycle to cycle. There is a scale, typically an electronic scale, in order to weigh the subject while the subject is in the chamber, and there may be some means for converting into a measure of mass the weight read out. From this, the controller or computer calculates the density of the subject, the percentage of body fat, and finally the lean body weight.

The system operates in accordance with Boyle's Law and Charles' Law. Boyle's Law states that for a given mass of gas at a constant temperature, pressure is inversely proportional to the volume. Charles' Law states that for a given mass of gas at a constant pressure, the volume is directly proportional to the temperature. These two laws can be combined to produce the Ideal Gas Law: $PV=nRT$, where P is the pressure, V is the volume, n is the mass of the gas, R is the universal gas constant, and T is the temperature. The Ideal Gas Law may be expressed in terms of volume: $V=(nRT)/P$.

Using a chamber of known volume, its volume can be decreased by a known amount and the pressure measured. From this pressure change the volume of the gas in the chamber can be determined, and this measured volume of gas subtracted from the known empty volume of the chamber will be equal to the volume of the object or person in the chamber. Further, there may be a scale attached to the floor of the chamber so that the weight of the subject can be determined while it is in the chamber. The weight can be converted to mass, and knowing the volume and the mass or weight, the density can be calculated through equations and/or lookup tables. For humans, body fat content can be determined based on density. For example, the volume would be calculated according to the formula $V=nRT/P$. Density, in grams per cubic centimeter (g/cc), is then determined by simply dividing the mass by the volume. The percentage of body fat may be calculated according to the formula:

% Body Fat = (495/density) − 450.

The lean body mass is then calculated by subtracting the percent body fat from the total mass. In order to change the volume of the chamber by a fixed, known, and repeatable amount according to this invention, there is used a balloon or some other inflatable and deflatable container such as a pleated container or a membrane. This novel approach provides an easy and economical way of changing the volume. Inside the chamber is a rigid, vented, fixed cavity. Inside this cavity is a balloon or other container. The balloon is inflated into the cavity, displacing the air in it to decrease the volume of the chamber, and is deflated to increase the volume of the chamber. On the surface of the vented cavity are sensors to sense when the balloon has totally filled the cavity. The balloon is mounted on a fixed support that allows the balloon to deflate to the same volume on every cycle. A compressor is used to inflate the balloon and valves cooperate with the compressor to inflate and to exhaust the balloon. A computer or other controller monitors or controls all of the functions. For example, when a person enters the chamber and closes the door, the computer may automatically turn on the compressor and start to inflate the balloon. When the computer senses that the balloon has totally filled the cavity, the compressor may be turned off, the pressure read, and the valves opened to empty the balloon. The mass of the person is measured and the density calculated. The computer takes into effect the pressure change, the mass, the temperature and the humidity. From that data is determined body fat content and lean body mass. The computer does all of this with a minimum of interaction from the user so that an unskilled operator can be employed to make the measurements with little or no training.

There is shown in FIG. 1 an aneroid volume determining system 10 according to this invention, which includes a chamber 12 and a volume adjuster 14. A subject 16 is placed in chamber 12 and a computer 18 directs volume adjuster 14 to increase the pressure, thereby decreasing the volume of air in chamber 12. The increase in pressure is sensed by pressure transducer 20 and communicated to computer 18. The weight of the subject is determined by scale 22 and may be converted to a figure of mass by weight-to-mass converter 24 before being directed to computer 18. The volume adjuster can then be recycled to its normal deflated condition so that the volume of air and the pressure in chamber 12 return to normal. The subject can then exit the chamber while computer 18 calculates the volume, the density, and the percentage of body fat which can be displayed or printed by peripheral device 26.

Figure 2:
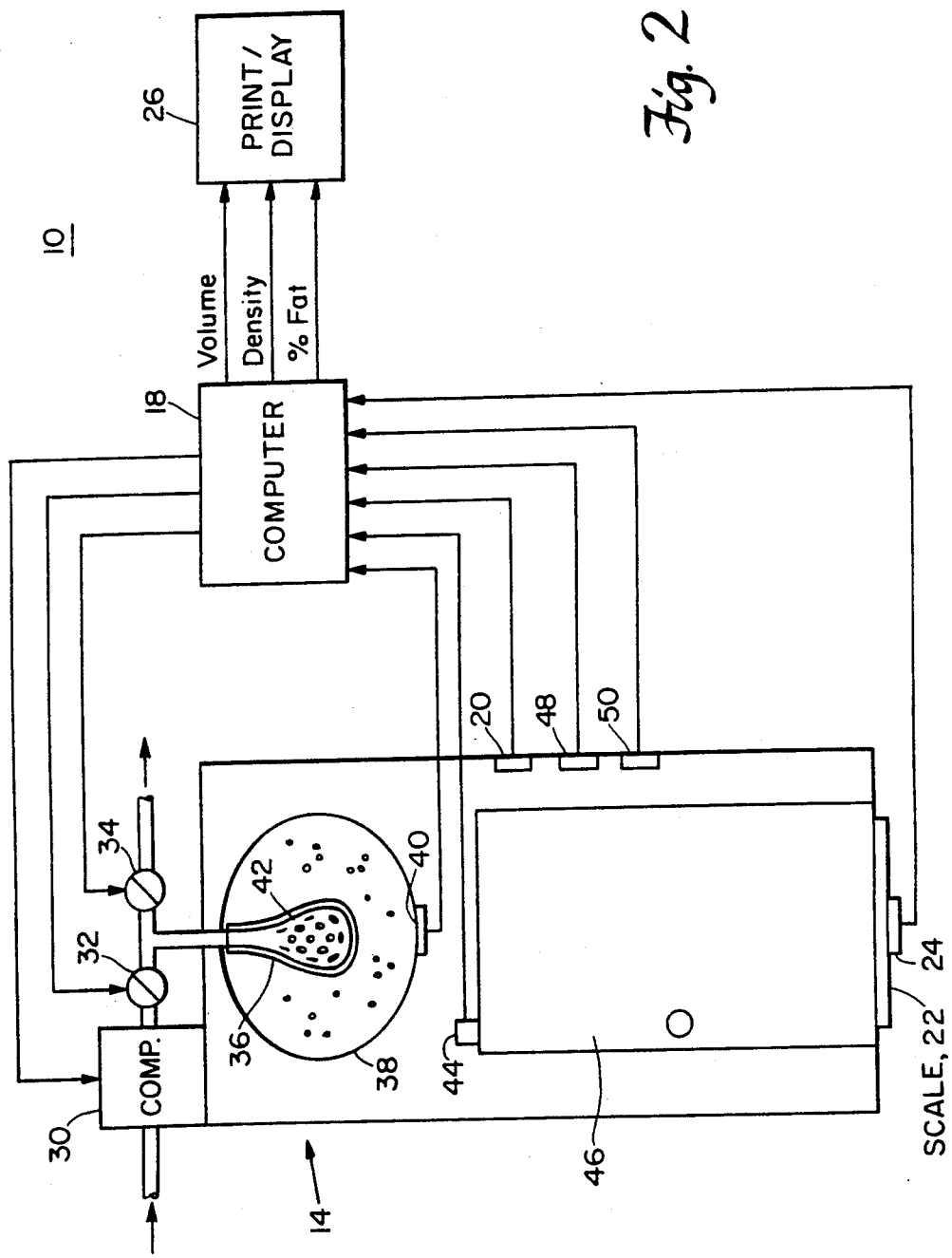
FIG. 2 is a more detailed schematic diagram of the chamber and volume adjuster of FIG. 1.

Volume adjuster 14, FIG. 2, may include a compressor 30, inlet valve 32, and an exhaust valve 34. Under control of computer 18, compressor 30 is turned on and valve 32 is opened while valve 34 is closed in order to inflate balloon 36. When inflation is complete, balloon 36 will have expanded fully to fill perforate cavity 38. The filled or inflated state of balloon 36 can be detected by fill sensor 40, and an indication of that is supplied to computer 18. The pressure may be read from pressure transducer 20 and the weight may be read from scale 22. Then compressor 30 is de-energized. Valve 32 is closed while valve 34 is opened, to cause balloon 36 to deflate to the condition in which it is shown in FIG. 2. There it has collapsed against support 42, which sets the minimum volume of the balloon in the deflated state. Holes in support 42 permit the air to pass through to inflate balloon 36. Computer 18 may be automatically actuated to initiate a cycle by door closed switch 44 operated after the subject has entered the chamber and securely closed door 46. Temperature and humidity may be detected by sensors 48 and 50 if desired.

Figure 3:
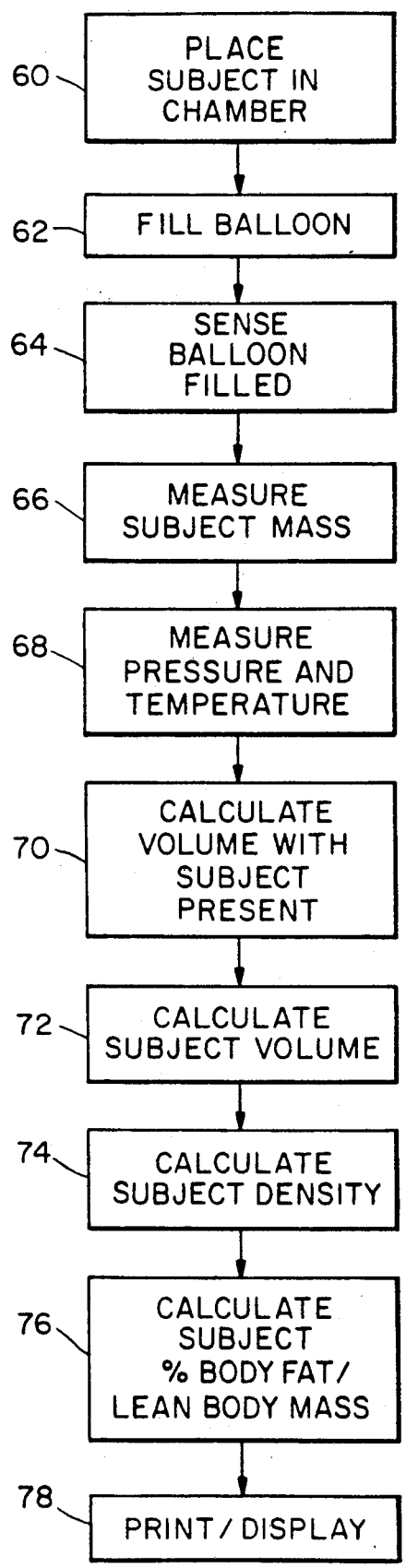
FIG. 3 is a flow chart showing the procedure supervised by the computer of FIGS. 1 and 2.

The computer is programmed as shown in FIG. 3 to carry out the procedure. In step 60, the subject is placed in the chamber. Then the balloon is filled in step 62 until it is sensed in step 64 that the balloon is completely filled. The subject's weight or mass is measured in step 66, and then the pressure and temperature are measured in step 68. The volume with the subject present is then calculated in step 70. Having calculated the volume with the subject present, and knowing the volume of the chamber initially without the subject present, the subject's volume can be calculated in step 72. Then using the weight or mass and the subject's volume, the subject's density can be calculated in step 74. From this the subject's percentage of body weight and lean body mass can be calculated in step 76, and the results printed or displayed in step 78.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An aneroid volume determining system comprising:
   an airtight chamber for holding a subject whose volume is to be detected;
   a volume adjuster including an inflatable container for varying the pressure in said chamber;
   means for sensing including a pressure transducer for sensing the pressure in said chamber in the deflated and inflated states of said container; and
   control means including means for calculating the volume of the subject in response to the detection, by said means for sensing, of the pressure in said chamber with and without the subject present in said chamber, and which control means provides control signals to said volume adjuster for automatically controlling the inflation and deflation of said container.

2. The aneroid volume determining system of claim 1 in which said volume adjuster includes a fixed cavity external to said container for defining the maximum volume of said container in the inflated state.

3. The aneroid volume determining system of claim 1 in which said volume adjuster includes a fixed support within said container for defining the minimum volume of said container in the deflated state.

4. The aneroid volume determining system of claim 1 in which said container is a balloon.

5. The aneroid volume determining system of claim 1 in which said volume adjuster includes pump means for inflating said container.

6. The aneroid volume determining system of claim 1 in which said volume adjuster includes valve means for controlling the inflating input to and deflating exhaust from said container.

7. The aneroid volume determining system of claim 1 further including a fill sensor for indicating when said container is fully inflated.

8. The aneroid volume determining system of claim 1 in which said means for sensing includes a temperature sensor for sensing the temperature in said chamber.

9. The aneroid volume determining system of claim 1 in which said means for sensing includes a humidity sensor for sensing the humidity in said chamber.

10. The aneroid volume determining system of claim 1 further including means for sensing the weight of the subject.

11. The aneroid volume determining system of claim 10 in which said means for sensing the weight of the subject includes means for converting the weight to mass.

12. The aneroid volume determining system of claim 11 in which said control means further includes means for calculating the density of said subject from the mass and volume.

13. The aneroid volume determining system of claim 12 in which said control means further includes means for calculating the percentage of body fat from the density.

14. The aneroid volume determining system of claim 13 in which said control means further includes means for calculating the lean body weight from the total mass and the percentage of body fat.

15. The aneroid volume determining system of claim 10 in which said control means further includes means for calculating the density of said subject from the weight and volume.

16. The aneroid volume determining system of claim 15 in which said control means further includes means for calculating the percentage of body fat from the density.

17. The aneroid volume determining system of claim 16 in which said control means further includes means for calculating the lean body weight from the total weight and the percentage of body fat.

* * * * *